US009839357B2

(12) United States Patent
Hübinette et al.

(10) Patent No.: US 9,839,357 B2
(45) Date of Patent: *Dec. 12, 2017

(54) DEVICE FOR ACQUIRING PHYSIOLOGICAL VARIABLES MEASURED IN A BODY

(71) Applicant: St. Jude Medical Coordination Center BVBA, Zaventem (BE)

(72) Inventors: Ulrik Hübinette, Alunda (SE); Magnus Samuelsson, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/064,875

(22) Filed: Mar. 9, 2016

(65) Prior Publication Data

US 2016/0183798 A1 Jun. 30, 2016

Related U.S. Application Data

(63) Continuation of application No. 12/562,364, filed on Sep. 18, 2009, now Pat. No. 9,301,699.

(51) Int. Cl.
*A61B 5/02* (2006.01)
*A61B 5/00* (2006.01)
(Continued)

(52) U.S. Cl.
CPC .......... *A61B 5/0024* (2013.01); *A61B 5/0002* (2013.01); *A61B 5/0008* (2013.01);
(Continued)

(58) Field of Classification Search
CPC ..... A61B 5/0024; A61B 5/0008; A61B 5/743; A61B 5/026; A61B 5/02141;
(Continued)

(56) References Cited

U.S. PATENT DOCUMENTS 5,417,222 A * 5/1995 Dempsey ............. A61B 5/0006
128/903
5,703,928 A 12/1997 Galloway et al.
(Continued)

FOREIGN PATENT DOCUMENTS

EP 0 712 603 A2 5/1996
EP 1 292 045 A2 3/2003
(Continued)

OTHER PUBLICATIONS

Australian Office Action dated Nov. 1, 2013, 3 pgs.
(Continued)

*Primary Examiner* — Meredith Weare
(74) *Attorney, Agent, or Firm* — Foley & Lardner LLP

(57) ABSTRACT

An eavesdropping arrangement for acquiring a measured physiological variable of an individual includes a receiver and a communication interface in a housing separate from the receiver. The communication interface is positioned along a communication link between a first sensor, which is configured to measure aortic blood pressure and to provide a signal representing measured aortic blood pressure, and a central monitoring device configured to monitor the measured aortic blood pressure. The communication interface includes a connection to the communication link that permits the communication interface to eavesdrop on the signal representing measured aortic blood pressure such that information representing measured aortic blood pressure is sent to the receiver while allowing the central monitoring device to receive and use the signal representing measured aortic blood pressure.

13 Claims, 5 Drawing Sheets

(51) Int. Cl.
*A61B 5/0215* (2006.01)
*A61B 5/0205* (2006.01)
*A61B 5/021* (2006.01)
*A61B 5/026* (2006.01)

(52) U.S. Cl.
CPC .......... *A61B 5/026* (2013.01); *A61B 5/02007* (2013.01); *A61B 5/02055* (2013.01); *A61B 5/02141* (2013.01); *A61B 5/02156* (2013.01); *A61B 5/02158* (2013.01); *A61B 5/6851* (2013.01); *A61B 5/743* (2013.01); *A61B 2560/0214* (2013.01); *A61B 2562/222* (2013.01)

(58) Field of Classification Search
CPC ............ A61B 5/02055; A61B 5/02158; A61B 5/6851; A61B 5/0002; A61B 5/02156; A61B 5/02007; A61B 2560/0214; A61B 2562/222
See application file for complete search history.

(56) References Cited

U.S. PATENT DOCUMENTS

| | | | |
|---|---|---|---|
| 5,871,451 A * | 2/1999 | Unger | A61B 5/0006 600/509 |
| 6,167,763 B1 | 1/2001 | Tenerz et al. | |
| 6,248,083 B1 | 6/2001 | Smith et al. | |
| 6,287,252 B1 | 9/2001 | Lugo | |
| 6,471,656 B1 * | 10/2002 | Shalman | A61B 5/0215 600/486 |
| 6,544,173 B2 | 4/2003 | West et al. | |
| 6,585,660 B2 | 7/2003 | Dorando et al. | |
| 6,615,067 B2 | 9/2003 | Hoek et al. | |
| 6,615,667 B2 | 9/2003 | Smith | |
| 6,705,992 B2 | 3/2004 | Gatzke | |
| 6,871,088 B2 | 3/2005 | Chinchoy | |
| 7,192,398 B2 | 3/2007 | Feliss et al. | |
| 7,803,121 B2 | 9/2010 | Plouf et al. | |
| 8,460,198 B2 | 6/2013 | Plouf et al. | |
| 8,639,319 B2 | 1/2014 | Hugh et al. | |
| 9,301,699 B2 * | 4/2016 | Hubinette | A61B 5/0002 |
| 2002/0013517 A1 | 1/2002 | West et al. | |
| 2002/0173724 A1 | 11/2002 | Dorando et al. | |
| 2004/0186524 A1 | 9/2004 | Chinchoy | |
| 2005/0275397 A1 | 12/2005 | Lightbody et al. | |
| 2005/0288559 A1 | 12/2005 | Feliss et al. | |
| 2007/0088221 A1 | 4/2007 | Stahmann | |
| 2007/0112274 A1 | 5/2007 | Heitzmann et al. | |
| 2008/0119758 A1 | 5/2008 | Samuelsson et al. | |
| 2008/0200770 A1 | 8/2008 | Hubinette | |
| 2009/0069714 A1 | 3/2009 | Eichmann et al. | |
| 2009/0131761 A1 | 5/2009 | Moroney, III et al. | |
| 2010/0168596 A1 | 7/2010 | Jaeschke et al. | |
| 2010/0198085 A1 * | 8/2010 | Knoll | A61B 5/0215 600/485 |

FOREIGN PATENT DOCUMENTS

| | | |
|---|---|---|
| EP | 1 774 905 A1 | 4/2007 |
| EP | 1 800 597 A2 | 6/2007 |
| EP | 1 922 988 A1 | 5/2008 |
| EP | 2 039 286 A1 | 3/2009 |
| JP | 39-086935 A | 3/1989 |
| JP | 64-086935 A | 3/1989 |
| JP | 07-213494 A | 8/1995 |
| JP | 08-280635 A | 10/1996 |
| JP | 09-062977 A | 3/1997 |
| JP | 10-071128 A | 3/1998 |
| JP | 2003-134030 A | 5/2003 |
| JP | 2003-525067 A | 8/2003 |
| JP | 2004-194996 A | 7/2004 |
| JP | 2004-528920 A | 9/2004 |
| JP | 2006-505294 A | 2/2006 |
| JP | 2008-126086 A | 6/2008 |
| JP | 2009-504357 A | 2/2009 |
| JP | 2010-534100 A | 11/2010 |
| JP | 2011-514826 A | 5/2011 |
| WO | WO-99/34724 A2 | 7/1999 |
| WO | WO-00/53081 A1 | 9/2000 |
| WO | WO-02/07595 | 1/2002 |
| WO | WO-2004/006761 | 1/2004 |
| WO | WO 2008104307 A1 * | 9/2008 ........... A61B 5/0215 |

OTHER PUBLICATIONS

European Office Action dated Apr. 16, 2015, 5 pages.
Japanese Office Action and English language translation dated Jun. 24, 2014, 5 pgs.
Japanese Office Action and English language translation dated Dec. 22, 2015, 5 pgs.
U.S. Office Action dated Oct. 24, 2013.
U.S. Office Action dated Feb. 8, 2012.
U.S. Office Action dated Apr. 10, 2015.
U.S. Office Action dated Jun. 19, 2014.
U.S. Office Action dated Aug. 1, 2012.
"Voltage Divider." http://en.wikipedia.org/wikiVoltage_divider.
"Universal Serial Bus." http://en.wikipedia.org/wiki/Universal_Serial_Bus.
Avolio, Alberto, "Central Aortic Blood Pressure and Cardiovascular Risk: A Paradigm Shift?", Hypertension, 2008; 51:1470-1471.
Canadian Office Action dated Oct. 18, 2016, 3 pages.
European Office Action dated Sep. 2, 2016, 4 pages.
Japanese Office Action and English translation, dated Mar. 28, 2017, 4 pages.

* cited by examiner

DEVICE FOR ACQUIRING PHYSIOLOGICAL VARIABLES MEASURED IN A BODY

CROSS-REFERENCE TO RELATED APPLICATIONS

This application is a continuation application of U.S. application Ser. No. 12/562,364, filed Sep. 18, 2009, the entire contents thereof is incorporated herein by reference.

TECHNICAL FIELD

The present invention relates to an eavesdropping device comprising a receiver and an interface for acquiring physiological variables measured in a body.

BACKGROUND ART

Today, there is an increased need for invasive measurements of physiological variables. For example, when investigating cardiovascular diseases, it is strongly desired to obtain local measurements of blood pressure and flow in order to evaluate the condition of the subject under measurement. Therefore, methods and devices have been developed for disposing a miniature sensor inside the body of an individual at a location where the measurements should be performed, and for communicating with the miniature sensor. Typically, the miniature sensor is arranged at a distal end of a guide wire, which is generally known in the art, and used for example in connection with treatment of coronary disease. The distal end of the guide wire is inserted into the body of a patient, for example into an opening into the femoral artery, and placed at a desired location. Once the guide wire is placed by the physician into the appropriate location, the miniature sensor can measure the blood pressure and/or flow. Measurement of blood pressure is a way to diagnose e.g. the significance of a stenosis. Further, a catheter of appropriate type may be guided onto the guide wire. Balloon dilation may then be performed. When measuring distal blood pressure ($P_d$), the sensor must be inserted into a vessel distal of the stenosis. For evident reasons, the dimensions of the sensor and the guide wire are fairly small; the guide wire typically has a diameter of 0.35 mm.

When diagnosing the significance of a stenosis in a hospital or a clinic, a catheter in connection with a first sensor is inserted into a patient proximal to a potential stenosis (typically visualized by means of flouroscopy). The sensor is connected to a central monitoring device via electrical leads. The central monitoring device used to monitor the patient's vital status, including blood pressure measured via the first sensor, is referred to as a cathlab monitor. In case of a stenosis, the vessel is narrower than normal, which impedes the flow of blood at the stenosis. When a narrowing of a vessel is seen on an angiogram, it is recommended that Fractional Flow Reserve (FFR) should be measured to determine the extent of the blood pressure difference proximal and distally of the stenosis.

FFR is approximated as $P_d/P_a$. The FFR is a measure of the pressure distal to a stenosis relative to the pressure proximal to the stenosis. Thus, FFR expresses vessel blood flow in the presence of a stenosis compared to the vessel blood flow in the hypothetical absence of the stenosis. Other physiological parameters may further be measured and transferred to the cathlab monitor. Should the FFR measurement show that there is a large drop in pressure in the vessel, treatment of the patient is required, for example by means of opening the vessel up with a balloon or stent, or by surgery for a coronary artery bypass.

To measure the distal blood pressure, the aortic blood pressure sensor is in prior art disconnected from the patient and the cathlab monitor. Then, a second sensor is used (which was discussed in the above) to measure $P_d$. This second sensor is inserted into the patient distal of the potential stenosis. The second sensor and the first sensor are connected to a small and easy-to-use monitoring device offering additional functionality. Thus, as can be seen in FIG. 3, pressure signals are connected to the smaller monitoring device 304 which in turn relays the pressure signals to the cathlab monitor 305.

This approach has drawbacks. For instance, connecting the smaller monitoring device to an up-and-running system requires disconnection of connectors carrying pressure signals to the cathlab monitor and reconnection of these connectors to the cathlab monitor via the smaller monitor. Further, in addition to the obviously tedious manual disconnecting operation, the disconnection of pressure signal connectors implies recalibrating the monitors, which is an undesired procedure.

SUMMARY OF THE INVENTION

To this end, there is provided an eavesdropping device for acquiring measured physiological variables of an individual, which eavesdropping device comprises a receiver and a communication interface.

The eavesdropping device of the present invention is typically applied in a system comprising a first sensor arranged to be disposed in the body of the individual for measuring aortic blood pressure $P_a$, and a second sensor arranged for measuring distal blood pressure $P_d$. Further, the system comprises a central monitoring device for monitoring the measured physiological variables and a communication link between the sensors and the central monitoring device for communicating signals representing the measured physiological variables from the sensors to the central monitoring device.

The eavesdropping device is configured such that the communication interface is arranged at the communication link to communicate at least the signal representing the aortic blood pressure to the receiver of the eavesdropping device. Moreover, the receiver of the eavesdropping device is connected to the communication link, in parallel with the central monitoring device, and arranged with at least one high-impedance input. The signal representing the aortic blood pressure $P_a$ is communicated to the high-impedance input via the communication interface, and the receiver of the eavesdropping device is further being arranged to receive the signal representing the measured distal blood pressure $P_d$ from the communication link. By means of the blood pressure signals of the respective sensor, FFR can be calculated.

The present invention is advantageous in that the central monitoring device, being for example a so called cathlab monitor, can be connected directly to the sensors by means of appropriate connecting means. Thereafter, the sensors and the central monitoring device are balanced, i.e. the aortic and distal blood pressure is zeroed respectively such that a correct pressure reference level is introduced in the measurement system. Now, once the balancing has been effected, the eavesdropping receiver, being for example a RadiAnalyzer®, can be connected to the communication link connecting the sensors to the central monitoring device, in parallel with the central monitoring device, via a high-impedance interface formed by the receiver and the communication interface of the eavesdropping device. That is, the eavesdropping receiver is able to "eavesdrop" on the communication link, thus being capable of accessing and monitoring the measured aortic blood pressure without affecting the pressure signal to any noticeable degree. In the prior art, as soon as a second monitoring device is to be connected between the sensors and the central monitoring device, connectors via which the pressure signals are supplied to the central monitor must be disconnected and coupled to the second monitor. Thereafter, the pressure signals are relayed from the second monitor to the central monitor. This prior art procedure requires a further balancing step to be undertaken; first, the sensors and the second monitor are balanced and second, the central monitor and the second monitor are balanced.

In an embodiment of the present invention, the communication link is arranged to communicate the signal representing measured aortic pressure via a wired connection to the central monitoring device, and via a wireless connection formed by the communication interface to the eavesdropping receiver. The signal representing measured distal blood pressure is communicated to the central monitoring device using either a wired or a wireless channel, and is communicated to the eavesdropping receiver using a wireless channel although a wired connection indeed can be used. As can be understood, various combinations are possible. It can also be envisaged that either, or both, of the measured pressure signals are communicated to the eavesdropping receiver using wired connections.

The distal pressure signals are preferably transported to the eavesdropping receiver using a wireless channel, while the aortic pressure signals preferably are transported to the eavesdropping receiver on a wireless channel to avoid further cabling, although it is still advantageous with respect to the prior art to transport the aortic pressure signals to the eavesdropping receiver using a wired connection.

However, in any selected combination the eavesdropping receiver is connected in parallel to the central monitoring device via a high-impedance communication interface of the eavesdropping device. Thus, the central monitoring device is, by appropriately using wired and/or wireless channels, connected and balanced to the two sensors, while the eavesdropping receiver is connected in parallel with the central monitoring device, via the high-impedance interface, without affecting the communicated aortic pressure signals. Hence, with these embodiments, the number of required steps involving calibration and reconnecting of cables are reduced. The connection of the eavesdropping receiver in parallel with the central monitoring device via a high-impedance communication interface clearly solves a number of prior art problems.

In a further embodiment of the present invention, the communication interface is supplied with power from the central monitoring device. In a further embodiment, the communication interface is arranged with a battery for power supply. In yet another embodiment, the battery can be charged from the central monitor.

In these embodiments, the (wireless or wired) communication interface can easily be connected by a user to the aortic sensor device and the central monitoring device by means of suitable connectors, without the user having to take into account powering of the communication interface. From a user's perspective, the supply of power is completely automated. Advantageously, the communication interface is premounted on a sensor cable which a user easily and straight-forwardly connects to the central monitor while initiating a measuring procedure.

A further advantage to have the eavesdropping receiver wirelessly connected to the communication link in parallel with the central monitoring device is that no cabling is necessary for the eavesdropping receiver.

The invention also includes various methods having one or more of the steps or actions or features described in this patent specification.

Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

The preferred embodiments of the present invention will be described in more detail with reference made to the attached drawings, in which.

DETAILED DESCRIPTION

In the prior art, it is known to mount a sensor on a guide wire and to position the sensor via the guide wire in a blood vessel in a living body to detect a physical parameter, such as pressure or temperature. The sensor includes elements that are directly or indirectly sensitive to the parameter. Numerous patents describing different types of sensors for measuring physiological parameters are assigned to the present assignee. For example, temperature can be measured by observing the resistance of a conductor having temperature sensitive resistance as described in U.S. Pat. No. 6,615,067. Another exemplifying sensor may be found in U.S. Pat. Nos. 6,167,763 and 6,615,667, in which blood flow exerts pressure on the sensor which delivers a signal representative of the exerted pressure. These U.S. patents are incorporated herein by reference for all the devices and methods described therein, including devices and methods for measuring a physical parameter.

In order to power the sensor and to communicate signals representing the measured physiological variable to a control unit acting as an interface device disposed outside the body, one or more cables for transmitting the signals are connected to the sensor, and are routed along the guide wire to be passed out from the vessel to an external control unit via a connector assembly. The control unit may be adapted for performing the functions of the previously mentioned signal conversion device, namely to convert sensors signals into a format accepted by the ANSI/AAMI BP22-1994 standard. In addition, the guide wire is typically provided with a central metal wire (core wire) serving as a support for the sensor.

Figure 1:
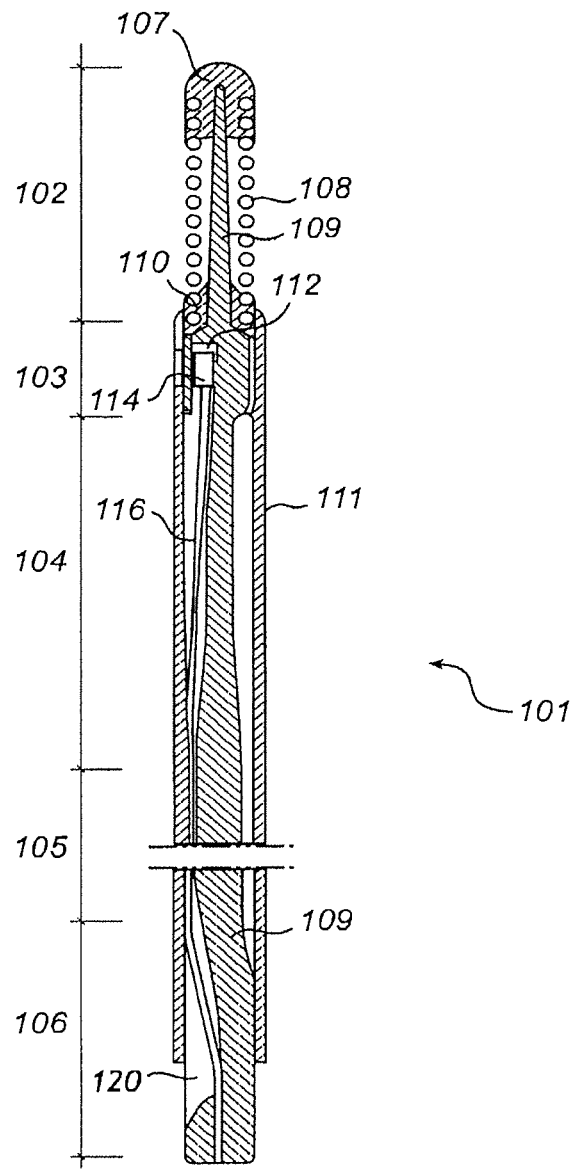
FIG. 1 shows a longitudinal section view of an exemplifying sensor guide construction that may be employed in the present invention.

FIG. 1 shows an exemplifying sensor mounted on a guide wire, i.e. a sensor guide construction 101. The sensor guide construction has, in the drawing, been divided into five sections, 102-106, for illustrative purposes. The section 102 is the most distal portion, i.e. that portion which is going to be inserted farthest into the vessel, and section 106 is the most proximal portion, i.e. that portion being situated closest to a not shown control unit. Section 102 comprises a radiopaque coil 108 made of e.g. platinum, provided with an arced tip 107. In the platinum coil and the tip, there is also attached a stainless, solid metal wire 109, which in section 102 is formed like a thin conical tip and functions as a security thread for the platinum coil 108. The successive tapering of the metal wire 109 in section 102 towards the arced tip 107 results in that the front portion of the sensor guide construction becomes successively softer.

At the transition between the sections 102 and 103, the lower end of the coil 108 is attached to the wire 109 with glue or alternatively, solder, thereby forming a joint 110. At the joint 110 a thin outer tube 111 commences which is made of a biocompatible material, e.g. polyimide, and extends downwards all the way to section 106. The tube 111 has been treated to give the sensor guide construction a smooth outer surface with low friction. The metal wire 109 is heavily expanded in section 103 and is in this expansion provided with a slot 112 in which a sensor element 114 is arranged, e.g. a pressure gauge. The sensor requires electric energy for its operation. The expansion of the metal wire 109 in which the sensor element 114 is attached decreases the stress exerted on the sensor element 114 in sharp vessel bends.

From the sensor element 114 there is arranged a signal transmitting cable 116, which typically comprises one or more electric cables. The signal transmitting cable 116 extends from the sensor element 114 to an (not shown) interface device being situated below the section 106 and outside the body. A supply voltage is fed to the sensor via the transmitting cable 116 (or cables). The signals representing the measured physiological variable are also transferred along the transmitting cable 116. The metal wire 109 is substantially thinner in the beginning of section 104 to obtain good flexibility of the front portion of the sensor guide construction. At the end of section 104 and in the whole of section 105, the metal wire 109 is thicker in order to make it easier to push the sensor guide construction 101 forward in the vessel. In section 106 the metal wire 109 is as coarse as possible to be easy to handle and is here provided with a slot 120 in which the cable 116 is attached with e.g. glue.

Figure 2:
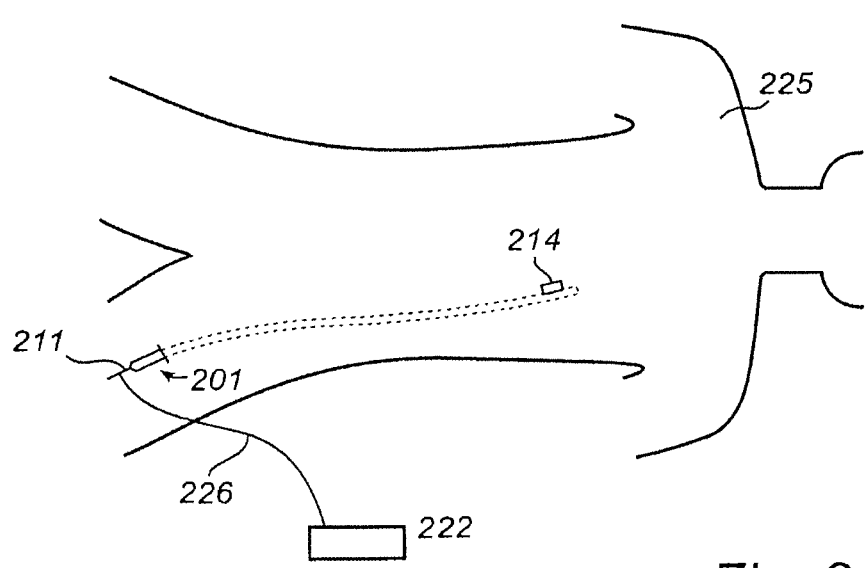
FIG. 2 shows a prior art sensor device for measuring a physiological variable in a body.

The use of a guide wire 201, such as is illustrated in FIG. 1, is schematically shown in FIG. 2. Guide wire 201 is inserted into the femoral artery of a patient 225. The position of guide wire 201 and the sensor 214 inside the body is illustrated with dotted lines. Guide wire 201, and more specifically electrically transmitting cable 211 thereof, is also coupled to a control unit 222 via a wire 226 that is connected to cable 211 using any suitable connector means (not shown), such as a crocodile clip-type connector or any other known connector. The wire 226 is preferably made as short as possible for easiness in handling the guide wire 201. Preferably, the wire 226 is omitted, such that the control unit 222 is directly attached to the cable 211 via suitable connectors. The control unit 222 provides an electrical voltage to the circuit comprising wire 226, cable 211 of the guide wire 201 and the sensor 214. Moreover, the signal representing the measured physiological variable is transferred from the sensor 214 via the cable 211 to the control unit 222. The method to introduce the guide wire 201 is well known to those skilled in the art. From the control unit 222, a signal representing distal pressure measured by the sensor 214 is communicated to one or more monitor devices, preferably using the ANSI/AAMI BP22-1994 standard, either by means of wireless communication or via a wired connection.

The voltage provided to the sensor by the control unit could be an AC or a DC voltage. Generally, in the case of applying an AC voltage, the sensor is typically connected to a circuit that includes a rectifier that transforms the AC voltage to a DC voltage for driving the sensor selected to be sensitive to the physical parameter to be investigated.

Figure 3:
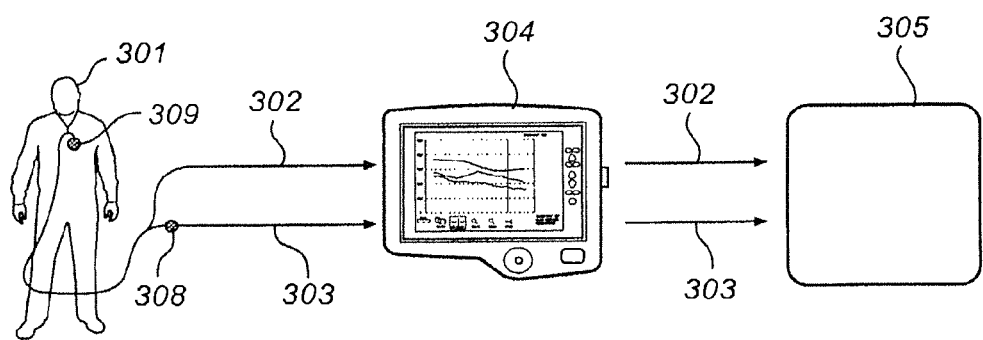
FIG. 3 illustrates how prior art measurements of FFR are undertaken using the sensor device discussed in connection with FIGS. 1 and 2.

FIG. 3 illustrates how measurements of FFR are undertaken today using the sensor discussed in connection with FIGS. 1 and 2. A first sensor 308 (not disposed in the patient) measures aortic blood pressure $P_a$ in known manner. A second sensor 309 is inserted into the patient 301 for measuring distal blood pressure $P_d$. A communication link comprising channel 302 for carrying the distal pressure and channel 303 for carrying the aortic pressure is arranged between the sensors and a second monitoring device 304, for example a RadiAnalyzer®. It should be noted, as is known in the art, that the RadiAnalyzer® is used to analyze the data received from one or both sensors and therafter display data to the user. The receiving function in the present invention can be coupled to or integrated into such a unit. From the second monitoring device 304, the respective channel is coupled to a central monitoring device 305 also referred to as a cathlab monitor. On one or both monitors, the two pressure types are used to calculate the FFR as $P_d/P_a$. Now, as previously has been discussed, the prior art approach has drawbacks; connecting the second, smaller monitoring device to an up-and-running system requires disconnection of connectors carrying pressure signals to the cathlab monitor and reconnection of these connectors to the cathlab monitor via the smaller monitor. Further, the disconnection of pressure signal connectors implies recalibrating of the monitors, which is an undesired step. First, the second monitoring device 304 must be calibrated with respect to the distal pressure channel 302. Second, the second monitoring device 304 must be calibrated with respect to the aortic pressure channel 303. Finally, the second monitoring device 304 and the first monitoring device 305 must be balanced, implying that both pressure channels 302, 303 running between the monitors is zeroed. This totals a number of four calibrating/balancing steps.

Figure 4:
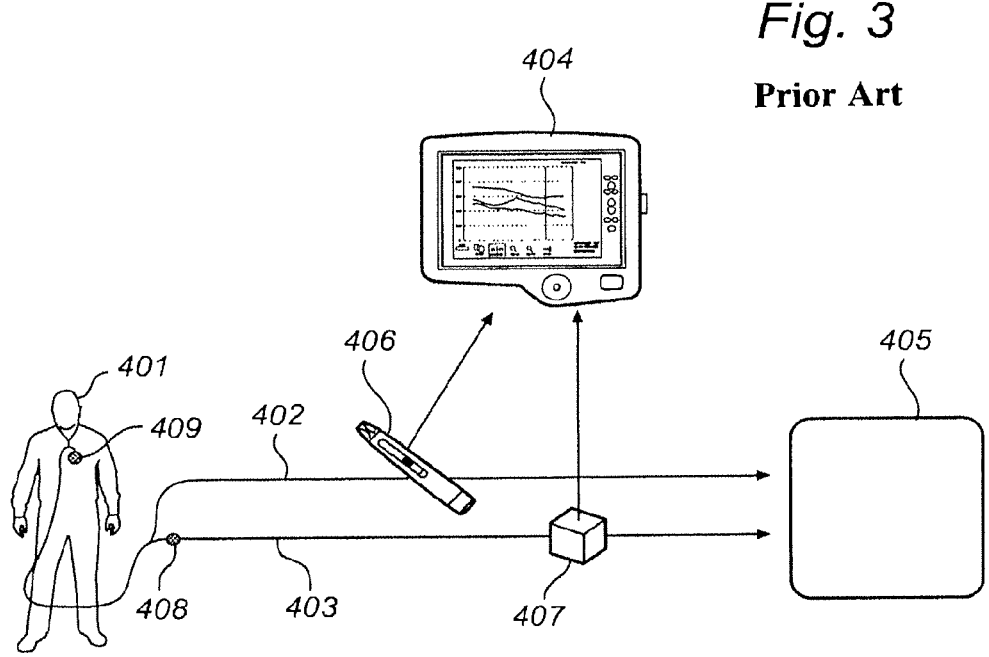
FIG. 4 shows an embodiment of the eavesdropping device of the present invention.

FIG. 4 shows an embodiment of the present invention mitigating mentioned problems in the prior art. In FIG. 4, distal pressure channel 402 carries the signal measured in patient 401 by internal sensor 409 via a wired connection through control unit 406. Control unit 406 can perform signal conditioning (to be described below) and send the distal pressure signal to an eavesdropping receiver 404 and central monitor 405. In another embodiment, signal conditioning can be performed by eavesdropping receiver 404 (in such an embodiment, functions of unit 406 are incorporated into the eavesdropping receiver and thus channel 402 is connected from the patient to the eavesdropping receiver and then from the receiver to monitor 405). A suitable control unit is a connector for a sensor guidewire assembly, such as the female connector for PressureWire®, however other control units can also be used. Thus, the signal representing measured distal pressure is transmitted to the eavesdropping receiver 404 and the central monitor 405 using wired distal pressure channel 402, and the signal representing aortic pressure measured by external sensor 408 in this particular embodiment is transferred to both the receiver 404 and the central monitor 405 using a wired channel 403. At an appropriate location along the aortic channel 403, for example at an input of the central monitoring device 405, a wired communication interface 407 of the inventive eavesdropping device is arranged. The eavesdropping interface 407 transmits the signal representing measured aortic pressure to the eavesdropping receiver 404. The interface 407 can electrically tap into a conductor in channel 403 via a high-impedance device (such as a resistor). Alternatively, the interface 407 can sense the electrical signal in channel 403 by sensing the magnetic and/or electric field in the vicinity of channel 403 that is created by the electrical signal passing through the conductor in channel 403. Since the eavesdropping interface 407 is arranged with a high-impedance input, the eavesdropping does not affect the signal carried over the aortic channel 403. Thus, with the eavesdropping device of the present embodiment, only three calibrating/balancing steps are required, since there is no need to calibrate the eavesdropped signal. Further, if the cathlab monitor is up-and-running, there is no need to make any disconnections in order to couple the eavesdropping monitor (i.e. typically a RadiAnalyzer®) to the central (cathlab) monitor. As can be seen from FIG. 4, the eavesdropping receiver 404 is connected to the communication link comprising distal channel 402 and aortic channel 403, in parallel with the central monitor 405, which greatly facilitates operation for the medical personnel.

The wired communication interface 407 is preferably pre-mounted on the standard communication cables for connecting an aortic pressure sensor 408 to a central monitor 405, such cables and connectors being known in the art, but can also be designed to be easily connectable to such cables, e.g. by providing an assembly comprising suitable connectors and the transmitting unit. In the latter event, the connectors of the aortic channel 403 to the central monitor 405 are disconnected and reconnected via the provided assembly. In such a procedure, reconnection of cables is necessary, however, no new calibration is needed.

Figure 5:
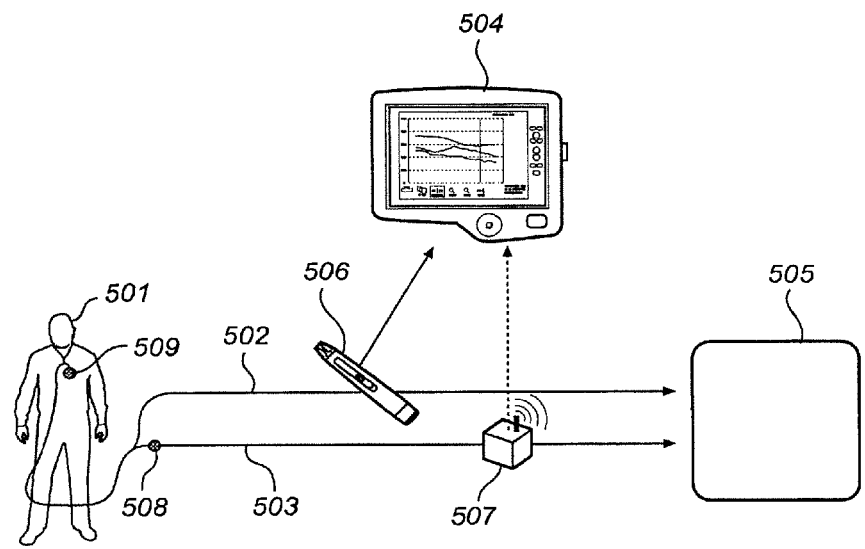
FIG. 5 shows a further embodiment of the eavesdropping device of the present invention.

FIG. 5 shows a further embodiment of the present invention mitigating mentioned problems in the prior art. In FIG. 5, distal pressure channel 502 carries the signal measured in patient 501 by internal sensor 509 via a wired connection through control unit 506. Thus, the signal representing measured distal pressure is transmitted to the eavesdropping receiver 504 and the central monitor 505 using wired distal pressure channel 502, and the signal representing aortic pressure measured by external sensor 508 in this particular embodiment is transferred to the central monitor 505 using a wired channel 503. At an appropriate location along the aortic channel 503, for example at an input of the central monitoring device 505, a wireless communication interface 507 of the inventive eavesdropping device is arranged. The wireless eavesdropping interface 507 transmits the signal representing measured aortic pressure to the eavesdropping receiver 504, which is capable of wireless communication. Since the eavesdropping interface 507 is arranged with a high-impedance input, the eavesdropping does not affect the signal carried over the aortic channel 503. Thus, with the eavesdropping device of the present embodiment, only three calibrating/balancing steps are required, since there is no need to calibrate the eavesdropped signal. Further, if the cathlab monitor is up-and-running, there is no need to make any disconnections in order to couple the eavesdropping receiver (i.e. typically a RadiAnalyzer®) to the central (cathlab) monitor. As can be seen from FIG. 5, the eavesdropping monitor 504 is connected to the communication link comprising distal channel 502 and aortic channel 503, in parallel with the central monitor 505, which greatly facilitates operation for the medical personnel.

Figure 6:
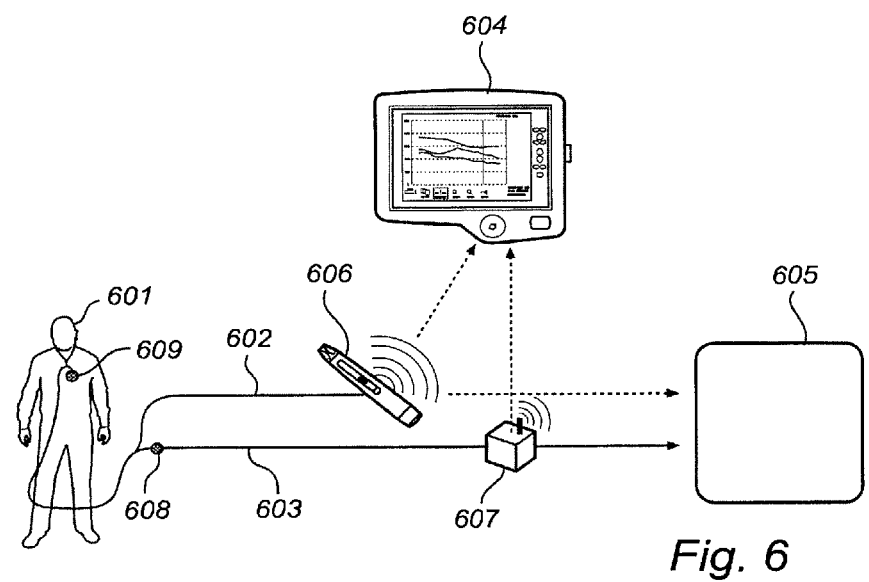
FIG. 6 shows another embodiment of the eavesdropping device of the present invention.

FIG. 6 shows another embodiment of the present invention mitigating mentioned problems in the prior art. In FIG. 6, distal pressure channel 602 carrying the signal measured in patient 601 by internal sensor 609 is wireless, which is enabled by means of control unit 606 transmitting in compliance with ANSI/AAMI BP22-1994. A suitable control unit is the control unit for Pressure Wire Aeris®, however other units may be used. Thus, the signal representing measured distal pressure is transmitted to the eavesdropping receiver 604 and the central monitor 605 using wireless distal pressure channel 602, while the signal representing aortic pressure measured by external sensor 608 in this particular embodiment is transferred to the central monitor 605 using a wired channel 603. As can be seen in FIG. 6, the central monitor is capable of wireless communication, possibly using a dongle attached to a monitor input and being adapted for communication with the control unit 606. At an appropriate location along the aortic channel 603, for example at an input of the central monitoring device 605, a wireless communication interface 607 of the inventive eavesdropping device is arranged. The wireless eavesdropping interface 607 transmits the signal representing measured aortic pressure to the eavesdropping receiver 604, which is capable of wireless communication. Since the eavesdropping interface 607 is arranged with a high-impedance input, the eavesdropping does not affect the signal carried over the aortic channel 603. Thus, with the eavesdropping device of the present embodiment, only three calibrating/balancing steps are required, since there is no need to calibrate the eavesdropped signal. Further, if the cathlab monitor is up-and-running, there is no need to make any disconnections in order to couple the eavesdropping receiver (i.e.

typically a RadiAnalyzer®) to the central (cathlab) monitor. As can be seen from FIG. 6, the eavesdropping receiver 604 is connected to the communication link comprising distal channel 602 and aortic channel 603, in parallel with the central monitor 605, which greatly facilitates operation for the medical personnel.

Figure 7:
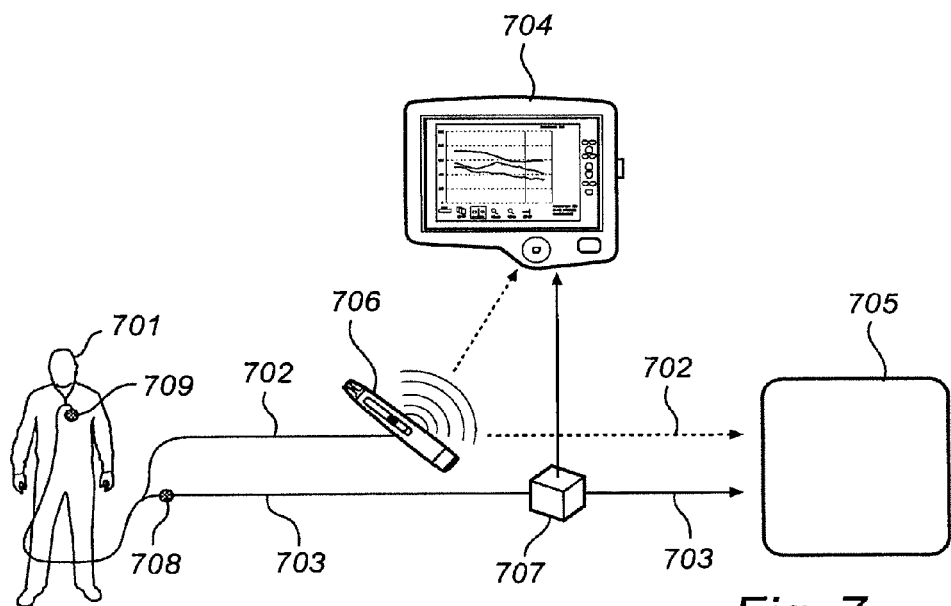
FIG. 7 shows still another embodiment of the eavesdropping device of the present invention.

FIG. 7 shows a further embodiment of the present invention mitigating mentioned problems in the prior art. In FIG. 7, distal pressure channel 702 carrying the signal measured in patient 701 by internal sensor 709 is wireless, which is enabled by means of control unit 706 transmitting in compliance with ANSI/AAMI BP22-1994. Thus, the signal representing measured distal pressure is transmitted to the eavesdropping receiver 704 and the central monitor 705 using a wireless portion of distal pressure channel 702, while the signal representing aortic pressure measured by external sensor 708 in this particular embodiment is transferred to the central monitor 705 as well as the eavesdropping receiver 704 using a wired channel 703. At an appropriate location along the aortic channel 703, for example at an input of the central monitoring device 705, a wired communication interface 707 of the inventive eavesdropping device is arranged. The eavesdropping interface 707 transmits the signal representing measured aortic pressure to the eavesdropping receiver 704. Since the eavesdropping interface 707 is arranged with a high-impedance input, the eavesdropping does not affect the signal carried over the aortic channel 703. Thus, with the eavesdropping device of the present embodiment, only three calibrating/balancing steps are required, since there is no need to calibrate the eavesdropped signal. Further, if the cathlab monitor is up-and-running, there is no need to make any disconnections in order to couple the eavesdropping receiver to the central monitor. As can be seen from FIG. 7, the eavesdropping receiver 704 is connected to the communication link comprising distal channel 702 and aortic channel 703, in parallel with the central monitor 705, which greatly facilitates operation for the medical personnel.

In the embodiments of the present invention shown in FIGS. 4-7, the communication interface may be supplied with power from the central monitoring device. Thus, the medical personnel can connect a cable on which the communication interface is arranged to the central monitoring device without having to think about coupling an external power supply to the communication interface. Alternatively, the communication interface is arranged with a battery for supply of power. Further, the communication interface can be arranged with a rechargeable battery, which may be charged by the central monitoring device.

Figure 8:
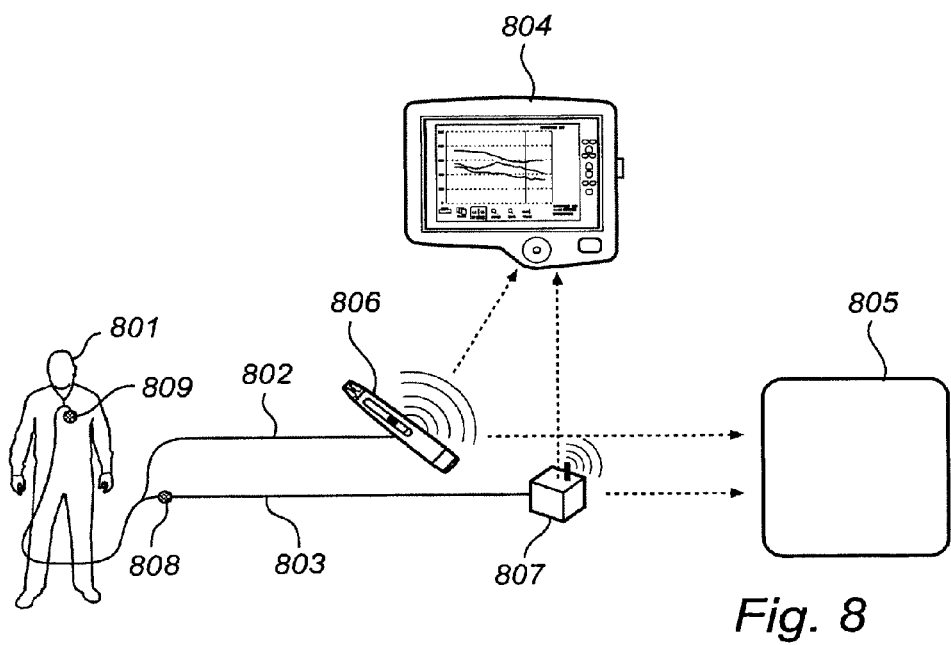
FIG. 8 shows yet a further embodiment of the eavesdropping device of the present invention.

FIG. 8 shows yet a further embodiment of the present invention mitigating mentioned problems in the prior art. In FIG. 8, signal distal pressure channel 802 carrying the signal measured in patient 801 by internal sensor 809 is wireless, which is enabled by means of control unit 806 transmitting in compliance with ANSI/AAMI BP22-1994. Thus, the signal representing measured distal pressure is transmitted to the eavesdropping receiver 804 and the central monitor 805 using a wireless portion of distal pressure channel 802. In this particular embodiment, the signal representing aortic pressure measured by external sensor 808 is transferred to the eavesdropping receiver 804 and the central monitor 805 using a wireless portion of channel 803. At an appropriate location along the aortic channel 803, a wireless communication interface 807 of the inventive eavesdropping device is arranged. The wireless eavesdropping interface 807 transmits the signal representing measured aortic pressure to the eavesdropping receiver 804 and the central monitoring device 805, which both are capable of wireless communication. The receiver and the central monitors can each use a dongle attached to a respective input and being adapted for wireless communication with the communication interface 807. Since the eavesdropping interface 807 is arranged with a high-impedance input, the eavesdropping does not affect the signal carried over the aortic channel 803. Thus, with the eavesdropping device of the present embodiment, again only three calibrating/balancing steps are required, since there is no need to calibrate the eavesdropped signal. Further, as previously mentioned, if the cathlab monitor is up-and-running, there is no need to make any disconnections in order to couple the eavesdropping receiver to the central monitor. As can be seen from FIG. 8, the eavesdropping receiver 804 is connected to the communication link comprising distal channel 802 and aortic channel 803, in parallel with the central monitor 805, which greatly facilitates operation for the medical personnel.

If the sensor inserted into the body of the individual is not compatible with the communication standard used by the cathlab monitor and other equipment used in connection with the FFR measurements made, which currently is the case in practice, the distal pressure signal is converted by a signal conversion unit arranged on the distal pressure channel of the communication link such that the converted signal, i.e. the output of the signal conversion unit, complies with the communication standard used. This has been described in the above, and the standard used for this type of equipment is normally ANSI/AAMI BP22-1994. The signal conversion unit is typically arranged at a guide wire connector.

Thus, the eavesdropping receiver is typically connected to the signal conversion unit, either by wire or wireless, for receiving the measured signal representing distal pressure. This requires calibration. For the aortic pressure, the eavesdropping receiver is connected to the aortic pressure channel of the communication link via a high-impedance input into the eavesdropping interface, thus making it possible for the receiver to eavesdrop on the aortic pressure channel. The eavesdropping does not require calibration.

Now, if in the future the sensor inserted into the body of the individual would become compatible with the communication standard used by the cathlab monitor and other equipment used in connection with the FFR measurements made, the distal pressure signal need not be converted by a signal conversion unit. In such a case, the eavesdropping receiver can be connected to both the aortic and distal pressure channel via a respective high-impedance input, either by means of wired or wireless connections. Consequently, it is possible for the receiver of the eavesdropping device to eavesdrop on the aortic and the distal pressure channel. Again, the eavesdropping does not require calibration. With such a configuration, the eavesdropping device of embodiments of the present invention would require only two calibration steps; the calibration of the distal and aortic pressure channels against the central monitoring device.

Even though the invention has been described with reference to specific exemplifying embodiments thereof, many different alterations, modifications and the like will become apparent for those skilled in the art. The described embodiments are therefore not intended to limit the scope of the invention.

The invention claimed is:

1. A system comprising:
a receiver configured to receive both (i) a signal representing a measured aortic blood pressure value measured by an aortic pressure sensor, and (ii) a signal representing a measured distal blood pressure value measured by a distal pressure sensor of a sensor guide wire, the receiver comprising a processor configured to calculate a metric indicating an extent of a stenosis in a blood vessel, the metric being based on at least the measured aortic blood pressure value and the measured distal blood pressure value, and a display configured to display said metric;
a communication interface configured to (i) receive a signal representing the measured aortic blood pressure value from the aortic pressure sensor via a wired connection between the aortic pressure sensor and the communication interface, and (ii) provide a signal representing the measured aortic blood pressure value to the receiver via a wireless connection between the communication interface and the receiver; and
a sensor guide wire connector configured to (i) receive a signal representing the measured distal blood pressure value via a connection between the distal pressure sensor and the sensor guide wire connector, and (ii) send a signal representing the measured distal blood pressure value to the receiver via a wired connection between the sensor guide wire connector and the receiver.

2. The system of claim 1, wherein the communication interface is configured to eavesdrop on the signal representing the measured aortic blood pressure value by electrically tapping into a conductor of a wired aortic channel at a location between the aortic pressure sensor and a monitoring device without affecting the measured aortic blood pressure value.

3. The system of claim 2, wherein the wired aortic channel comprises a standard communication cable for connecting the aortic pressure sensor to the monitoring device, and the communication interface is pre-mounted on the standard communication cable.

4. The system of claim 2, wherein the wired aortic channel comprises a standard communication cable for connecting the aortic pressure sensor to the monitoring device, and the communication interface is connectable to the standard communication cable such that connectors of the wired aortic channel to the monitoring device can be disconnected and reconnected via the communication interface.

5. The system of claim 1, wherein the communication interface is configured to eavesdrop on the signal representing the measured aortic blood pressure value by sensing at least one of a magnetic field or an electric field in the vicinity of a wired aortic channel at a location between the aortic pressure sensor and a monitoring device without affecting the measured aortic blood pressure value.

6. The system of claim 5, wherein the wired aortic channel comprises a standard communication cable for connecting the aortic pressure sensor to the monitoring device, and the communication interface is pre-mounted on the standard communication cable.

7. The system of claim 5, wherein the wired aortic channel comprises a standard communication cable for connecting the aortic pressure sensor to the monitoring device, and the communication interface is connectable to the standard communication cable such that connectors of the wired aortic channel to the monitoring device can be disconnected and reconnected via the communication interface.

8. The system of claim 1, wherein the communication interface includes at least one battery for supply of power.

9. The system of claim 8, wherein the communication interface is configured such that the at least one battery is chargeable via a monitoring device.

10. The system of claim 1 wherein the communication interface is configured to be supplied with power from a monitoring device.

11. The system of claim 1, wherein the sensor guide wire connector is further configured to send a signal representing the measured distal blood pressure value to a monitoring device.

12. The system of claim 11, wherein the sensor guide wire connector is configured to send a signal representing the measured distal blood pressure value to the monitoring device via a wired connection between the sensor guide wire connector and the monitoring device.

13. The system of claim 1, wherein the metric indicating an extent of a stenosis in a blood vessel is Fractional Flow Reserve (FFR).

* * * * *